United States Patent
Perry

(10) Patent No.: US 7,238,375 B1
(45) Date of Patent: Jul. 3, 2007

(54) COMPOSITION AND METHOD TO PROMOTE HUMAN HAIR GROWTH

(76) Inventor: Stephen C. Perry, 90 Kerry Pl., Suite 2, Norwood, MA (US) 02062

( * ) Notice: Subject to any disclaimer, the term of this patent is extended or adjusted under 35 U.S.C. 154(b) by 0 days.

(21) Appl. No.: 10/905,168

(22) Filed: Dec. 20, 2004

(51) Int. Cl.
*A61K 36/16* (2006.01)

(52) U.S. Cl. .................. 424/727; 424/522; 424/630; 424/752; 514/63; 562/563; 562/559

(58) Field of Classification Search .............. None
See application file for complete search history.

(56) References Cited

U.S. PATENT DOCUMENTS

| | | | |
|---|---|---|---|
| 2,431,558 A | 11/1947 | Huber | |
| 4,713,397 A | 12/1987 | Hirama et al. | |
| 4,847,260 A | 7/1989 | Abe | |
| 4,968,685 A | 11/1990 | Grollier | |
| 5,025,026 A | 6/1991 | Osamu | |
| 5,043,162 A | 8/1991 | Trager | |
| 5,069,898 A | 12/1991 | Goldberg | |
| 5,133,958 A | 7/1992 | Stuckler | |
| 5,143,925 A | 9/1992 | Shander et al. | |
| 5,256,678 A | 10/1993 | Nakaguchi | |
| 5,328,914 A * | 7/1994 | Hocquaux et al. | 514/310 |
| 5,407,675 A | 4/1995 | Etemad-Moghadam | |
| 5,422,100 A | 6/1995 | Eliaz et al. | |
| 5,490,980 A | 2/1996 | Richardson et al. | |
| 5,525,336 A | 6/1996 | Green et al. | |
| 5,663,160 A * | 9/1997 | Meybeck et al. | 514/182 |
| 5,744,128 A * | 4/1998 | Holick | 424/60 |
| 5,750,108 A | 5/1998 | Edwards | |
| 5,972,345 A * | 10/1999 | Chizick et al. | 424/727 |
| 6,001,378 A * | 12/1999 | Desjonqueres | 424/401 |
| 6,017,893 A * | 1/2000 | Segelman | 514/27 |
| 6,063,389 A * | 5/2000 | Chevalier et al. | 424/401 |
| 6,375,948 B1 | 4/2002 | Tsuji et al. | |
| 6,376,557 B1 | 4/2002 | Zaveri | |
| 6,596,266 B2 * | 7/2003 | Catalfo et al. | 424/74 |
| 7,186,279 B2 * | 3/2007 | Palpu et al. | 8/405 |
| 2003/0082130 A1 * | 5/2003 | Verdun et al. | 424/70.13 |

FOREIGN PATENT DOCUMENTS

JP 2002-097116 A * 4/2002

OTHER PUBLICATIONS

CAPLUS English abstract of IT 1299262 (2000).*

* cited by examiner

*Primary Examiner*—Susan Hoffman
(74) *Attorney, Agent, or Firm*—Malin, Haley & DiMaggio, P.A.

(57) ABSTRACT

This invention relates to a composition of matter for producing hair growth and preventing hair loss in humans and the method for using said composition. The composition comprises four complexes and a carrier liquid, mixed together and added to any topical treatment or produced as an ingestible dietary supplement. Complexes 1, 2, and 3 are comprised of substances that prevent hair loss while Complex 4 promotes hair growth. Complex 1 is comprised of octyl butyrate and glutaminpeptides. Complex 2 comprises a mixture of minerals, plant extracts, vitamin B6, and linolenic acid. Complex 3 comprises a mixture of *Ginkgo biloba* extract, emu oil, a source of silicon, and a blend of amino acids. Complex 4 comprises a mixture of several plant extracts. The product should be used by the consumer at regular intervals, preferably 5 to 7 times per week in the form of a serum.

13 Claims, 3 Drawing Sheets

Figure 2

|   | Day 0 | | Day 90 | |
| --- | --- | --- | --- | --- |
| Volunteer | Telogen | Anagen | Telogen | Anagen |
| 1 | 8 | 43 | 10 | 41 |
| 2 | 10 | 39 | 8 | 41 |
| 3 | 17 | 26 | 13 | 30 |
| 4 | 12 | 36 | 4 | 45 |
| 5 | 8 | 37 | 3 | 44 |
| 6 | 10 | 27 | 10 | 29 |
| 7 | 12 | 36 | 6 | 41 |
| 8 | 11 | 65 | 8 | 68 |
| 9 | 13 | 36 | 9 | 41 |
| Mean | 11.22 | 38.33 | 7.89 | 42.22 |
| SEM | 2.77 | 11.36 | 3.14 | 11.21 |

Figure 3

|   | Day 0 | | Day 90 | |
| --- | --- | --- | --- | --- |
| Volunteer | Telogen | Anagen | Telogen | Anagen |
| 11 | 5 | 36 | 3 | 38 |
| 12 | 6 | 65 | 7 | 67 |
| 13 | 10 | 44 | 8 | 46 |
| 14 | 8 | 44 | 9 | 45 |
| 15 | 4 | 41 | 4 | 43 |
| 16 | 7 | 39 | 3 | 42 |
| 17 | 3 | 37 | 5 | 35 |
| 18 | 4 | 40 | 2 | 41 |
| 19 | 10 | 46 | 6 | 49 |
| Mean | 6.33 | 43.56 | 5.22 | 45.11 |
| SEM | 2.60 | 8.71 | 2.44 | 9.21 |

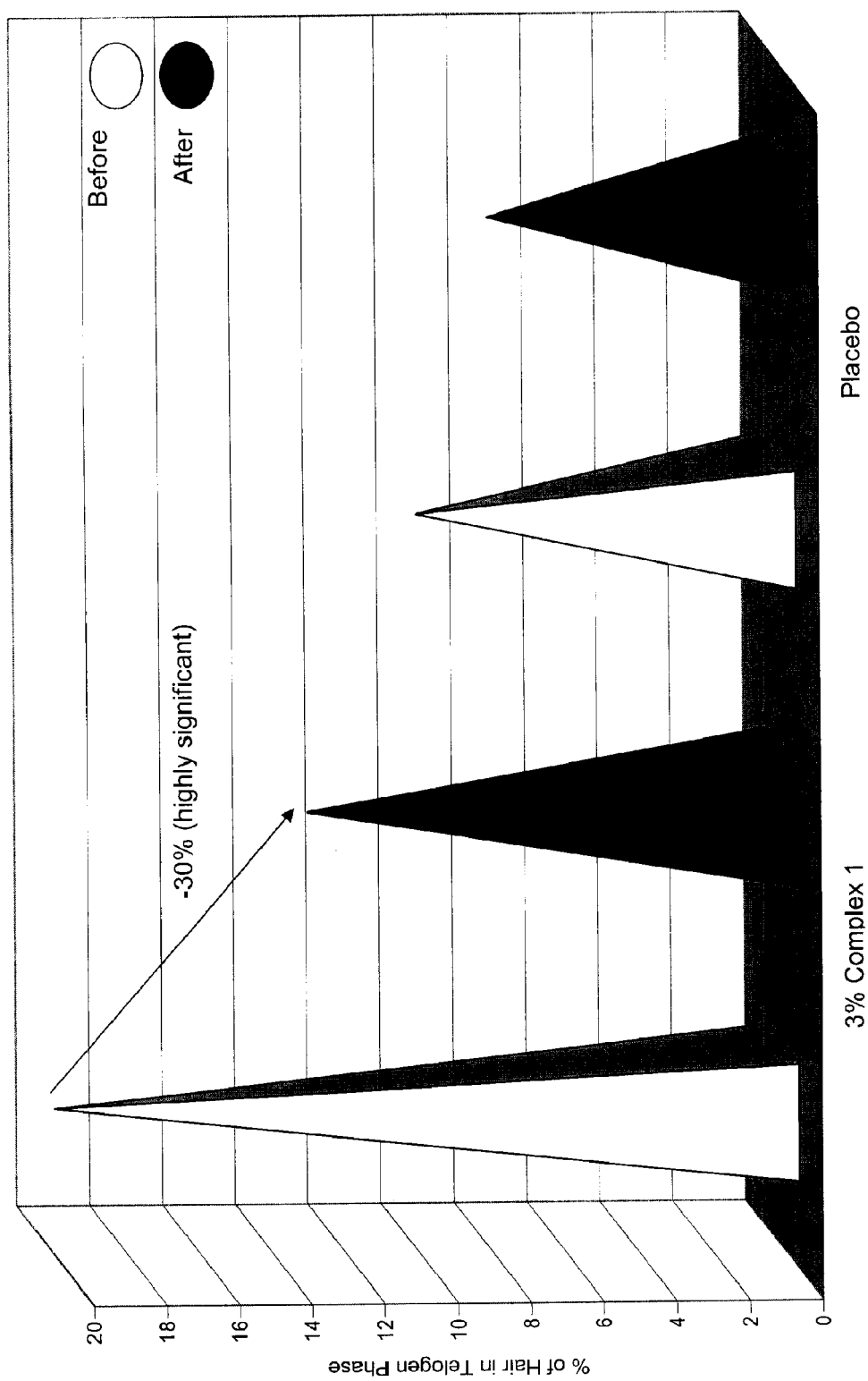

COMPOSITION AND METHOD TO PROMOTE HUMAN HAIR GROWTH

FIELD OF THE INVENTION

This invention relates to a composition of matter for producing hair growth and preventing hair loss in humans and the method for making said composition.

DESCRIPTION OF RELATED ART

Hair loss is an age-old condition suffered by millions of men and women, albeit more commonly by men. Human hair loss has numerous causes, ranging from psychological stress to hormonal influences to chemical and physical trauma, such as from certain medications or from trichotillomania (compulsive hair pulling). However, the single largest cause of human hair loss is androgenic alopecia, which is not well understood, but may be hereditary in nature. Alopecia occurs when the pilar cycle, which breaks down the life of a hair into three phases, is accelerated or disrupted. The growth phase of a hair is called the anagen phase while the final stage of the pilar cycle when the hair falls out is called the telogen phase. A detailed description of the pilar cycle and androgenic alopecia can be found in U.S. Pat. No. 5,750,108, issued to Edwards on May 12, 1998. Due to the great prevalence of human hair loss, products to avoid the results of premature alopecia have become a major aim of cosmetic research.

Numerous patents in the prior art describe compositions and methods for the prevention of hair loss and the stimulation of hair growth. Some of these inventions make use of mixtures of hair-absorbable and hair-absorbable bulking agents and scalp stimulating compositions (U.S. Pat. No. 5,069,898, issued to Goldberg on Dec. 3, 1991), or use various nicotinates as vasodilators (U.S. Patent Nos. 2,431,558, issued to Huber on Nov. 25, 1947; 4,847,260, issued to Abe et al., on Jul. 11, 1989; 4,968,685, issued to Grollier on Nov. 6, 1990; 5,025,026, issued to Osamu on Jun. 18, 1991; 5,043,162, issued to Trager on Aug. 27, 1991; 5,256,678, issued to Nakaguchi on Oct. 26, 2003). Other products have used combinations of nicotinic esters and pyrimidine derivatives, such as vitamin B6 (U.S. Pat. Nos. 5,133,958, issued to Stuckler on Jul. 28, 1992; 5,157,036, issued to Grollier on Oct. 20, 1992). In U.S. Pat. No. 4,713,397, issued to Hirama et al., on Dec. 15, 1997, a mixture of a vasodilator and a ubiquinone was used to reduce hair loss in humans. Treatments describing the topical application of herbal extracts are also found in the prior art. U.S. Pat. No. 5,422,100, issued to Eliaz et al., on Jun. 6, 1995.

Transglutaminase, an enzyme produced in keratinocytes and found in the hair follicles and epidermis of humans, is known to prevent hair loss. This enzyme aids in the formation of dipeptide bonds between residues of the amino acids lysine and glutamine found in structural proteins. This bonding is necessary for the formation of corneocyte envelopes during the keratinisation process that occurs in the hair follicle and in the epidermis. The bonds induced by transglutaminase stabilize the epidermis and also the base of the hair where it is attached to the scalp, thereby increasing the hair's physical resistance to external stressors and to internal proteolysis. (Podlodowski, R. R. and L. A. Goldsmith, Physiology, Biochemistry and Molecular Biology of the Skin (1991)). Certain glutamine-rich proteins, such as involucrine, are particularly important in the formation of the cutaneous barrier, and therefore, are important as well to a hair's resistance to chemical and physical injury. (Rice, R. H. and H. Green, Cell, 18:681-694 (1979)). The cross-linking that occurs when transglutaminase catalyzes bonding between polypeptides results in reticulation of proteins, such as trichohyaline, found in a hair's internal root sheath. This protein reticulation acts to protect the hair from physical and chemical damage caused by both external and internal sources.

Sodium butyrate has been shown to stimulate the synthesis of transglutaminase in keratinocytes and also promotes the formation of the corneocyte envelope during the terminal differentiation stage of a hair. (Schmidt, R. et al., J. of Cellular Physiology, 140:281-287 (1989)). However, sodium butyrate is not useable in cosmetic applications due to its strong unpleasant odor. Researchers have determined that octyl butyrate, an ester of octanol and butyric acid, mimics the beneficial effects of sodium butyrate. Octyl butyrate is inodorous, and is easily hydrolyzed by esterase enzymes in the skin, which frees butyrate in situ. (Wiseman, M. et al., Int. J. Cancer, 46:462-467 (1990)). In U.S. Pat. No. 6,376,557, issued to Zaveri on Apr. 23, 2002, a composition and method for treating alopecia is described wherein one component comprises a mixture of octyl butyrate and glutamine-containing peptides at 0.5 to 4.0% by weight of the composition, in addition to numerous other chemicals and plant extracts.

In U.S. Pat. No. 5,143,925, issued to Shander et al., on Sep. 1, 1992, an inhibitor of transglutaminase activity is described that can be topically applied to reduce the rate of hair growth and to alter the character of androgen-stimulated hair growth by rendering the hair more vellus-like. Another invention in the prior art describes a composition containing an active ingredient that is beneficial to the skin and transglutaminase. U.S. Pat. No. 5,490,980, issued to Richardson et al., on Feb. 13, 1996. In that invention, the active ingredient must contain an amine moiety that can be crosslinked to glutamine residues in the hair and skin by the catalytic action of transglutaminase. Additionally, U.S. Pat. No. 5,525,336, issued to Green et al., on Jun. 11, 1996, describes a composition comprised of transglutaminase and one or more corneocyte envelope proteins, which form a protective layer on the hair. In that invention, transglutaminase acts as a crosslinking agent to induce the formation of peptide bonds between the corneocyte envelope proteins, thereby creating a protective layer on the hair to provide protection from chemical or physical injury. Another invention in the prior art, U.S. Pat. No. 6,375,948, issued to Tsuji et al., on Apr. 23, 2002, describes a method for suppressing hair growth that uses an endopeptidase inhibitor that impedes the hair growth effect of transglutaminase.

Another method of hair loss prevention uses anti-androgen compounds as DHT blockers to prevent hair loss in humans. DHT, or dihydrotestosterone, is produced when the enzyme 5-alpha-reductase reduces testosterone to one of two forms. Type 1 5-alpha-reductase represents a cutaneous form of the enzyme, which is located primarily in the skin's sebocytes, but that is also found in epidermal and follicular keratinocytes, dermal papilla cells, sweat glands, and in fibroblasts. Type 2 5-alpha-reductase is located in the seminal vesicles and prostate gland in men, and in the inner root sheath of hair follicles in both sexes. Researchers have determined that the DHT which harms human hair follicles originates in the skin's sebocytes and sweat glands. (Chen, W. et al., "The 5-alpha-reductase system and its inhibitors: Recent development and its perspective in treating androgen-dependent skin disorders," Dermatology, 193(3):177-184 (1996)). Thus, the DHT that is harmful to human hair follicles is produced as a result of the enzymatic actions of Type 1 5-alpha-reductase in sebocytes and sweat glands. However, drugs, such as Propecia® (Finasteride) have a greater affinity for Type 2 DHT and are marketed to address DHT-induced hair loss as well as to control prostate enlargement. Several disadvantages exist to the use of Propecia®, one being that it must be administered orally through the ingestion of pills that dissolve to release the drug throughout the body, and another major disadvantage being that it can only be used by males due to its serious side effects on women and fetuses.

Copper ion has been determined to be an extremely effective inhibitor of both Type 1 and Type 2 5-alpha-reductase. In addition, copper ion can be applied topically, which is an advantage over oral medications. The application of copper ion to skin results in a 50% reduction in activity of Type 1 5-alpha-reductase at 1.9 micromolar (0.12 micrograms copper ion per milliliter) and for Type 2 5-alpha-reductase at 10.2 micromolar (1.2 micrograms copper ion per milliliter). (Sugimoto, Y. et al., "Cations inhibit specifically type 15-alpha-reductase found in human skin," J. of Investigative Dermatology, 104(5):775-778 (1995)). Copper ion is the only metal to exhibit the 5-alpha-reductase inhibiting effect. While the level of active copper ion free to inhibit 5-alpha-reductase in the human body is low (1.0 microgram per milliliter in the blood and less in the skin), research has revealed that copper peptides applied to the skin can raise the level of copper ion to the effective level of 1.0 microgram per milliliter.

Additionally, the berries of red saw palmetto (*Serenoa repens*), a small palm native to the southeastern United States, possess chemicals that also inhibit the activity of 5-alpha-reductase, thereby preventing the formation of DHT that can bind to androgen receptors. The usage of saw palmetto berry extract has been previously described in U.S. Pat. No. 5,750,108, wherein a hair treatment kit was provided comprising a first treatment of tea tree oil, a second treatment of chlorine dioxide, and the third treatment being saw palmetto berry extract. In Europe, the extract of red saw palmetto is called Permixon and is used to treat prostate hyperplasia by processes similar to those found in finasteride, which is also used to treat prostate conditions. The extract blocks 50% of the uptake of DHT at its target tissue receptor sites. The berries contain an oil comprised of several fatty acids, including caprice, acrylic, laurel, oleic, and palmitic acids, as well as the ethyl esters of these fatty acids. The berries also contain high levels of phytosterols, including beta-sitosterol, cycloartenol, stigmaterol, lupeol, lupenone, and 24-methyl-cycloartneol, as well as other oils, resins, and tannins.

Similarly, extracts from pygeum bark (*Pygeum africanum*) and nettle root (*Urtica dioica*), which are also used to treat prostate hyperplasia, also act to inhibit production of DHT within the body. The extracts of these two plants inhibit the action of 5-alpha-reductase and aromatase, both of which are critical to the production of DHT. The use of nettle extract as a rubefacient has been described previously in U.S. Pat. Nos. 5,133,958, 5,407,675, issued to Etemad-Moghadam on Apr. 18, 1995, and U.S. Pat. No. 5,750,108. Nettle and pygeum extracts have been shown to have a synergistic effect when taken together, and a combination of these extracts is sold in Europe under the name "Prostaitin." The combination is also believed to have similar positive effects on hair growth as does the extract of red saw palmetto. (Hartman, R. W., et al., Phytomedicine, 3:121-128 (1996)).

Silicon, never found in its pure form, is a nonmetallic element upon which the quality and quantity of hair depends. Silicon found in orthosilicic acid is the only form of silicon that humans can effectively use, and is present naturally in the bloodstream. When the concentration of orthosilicic acid in water becomes too high, silica forms. Silica is a polymeric silicon-hydroxide-oxide-water complex. Silica polymers that can be broken down into single units of silicon during digestion produce the only silica that can be used by humans. Therefore, silica gel, colloidal silica, silicates, clays, and most foods and herbal extracts, which contain silica rather than orthosilicic acid, are not good sources of silicon for the human body. Silicon, which is found in the dermis, epidermis, and hair, is involved in the metabolic functions of the scalp, downy areas, and glabrous area. In U.S. Pat. No. 6,376,557, a composition is described for the prevention of hair loss that contains a 20% solution of dimethylsilanediol salicylate in butylene glycol with thiethanolamine. This component of the composition is obtained by the mild hydrolysis of dimethylsilyl salicylate, and is present in the composition from approximately 3.0 to 4.0% by weight.

Although the foregoing compositions have exhibited positive effects on the scalp in preventing hair loss and in promoting hair growth, the majority are meant to be applied topically to the hair or scalp, and most attack only certain causes of hair loss without acting to promote the growth of hair.

SUMMARY OF THE INVENTION

The invention comprises a mixture of four complexes and a carrier liquid, which taken together are effective at preventing hair loss and promoting hair growth. The composition can be applied topically in the form of a serum, shampoo, gel, or conditioner, or can be produced as an ingestible dietary supplement.

Complex 1, a novel composition comprised of octyl butyrate and glutaminpeptides, prevents hair loss both by inducing the synthesis of the enzyme transglutaminase and by providing a substrate upon which the transglutaminase can act to crosslink structural proteins in the hair, thereby increasing the hair's resistance to external and internal injury. The structural proteins in hair are crosslinked when transglutaminase forms peptide bonds between the glutamine and lysine residues of the proteins forming the hair.

Complex 2 is comprised of a mixture of copper ion, red saw palmetto extract, pygeum extract, nettle extract, zinc, vitamin B6, and linolenic acid, all of which have demonstrated excellent hair loss preventative properties. These ingredients prevent hair loss by reducing the binding of DHT to testosterone receptor sites in the skin and hair follicle, thereby inhibiting DHT's harmful effects.

Complex 3 is comprised of a mixture of *Ginkgo biloba* extract, cysteine, emu oil, a novel source of biologically-useful silicon, and a blend of amino acids, including taurine, methionine, and glutathione. The components of Complex 3 work to prevent hair loss by providing an abundant source of structural materials (sulfur-containing amino acids and silicon) used in the generation of a hair as well as by inhibiting 5-alpha-reductase's synthesis of DHT.

Complex 4, comprised of mixture of extracts of bergamot, jaborandi, southernwood, and nettle, constitutes the hair growth component of the invention. All of these plant-derived compounds have been demonstrated to stimulate the growth of hair in humans.

The four complexes are mixed together and can be added to any topical treatment, such as a shampoo, conditioner, styling product, or serum, or can be ingested in the form of a dietary supplement, such as a caplet, tablet, capsule, lozenge, or drink. The product should be used by the consumer at regular intervals twice each day for the first 7 days and then preferably 5 to 7 times per week, and more preferably 7 times per week.

An object of this invention is to prevent hair loss and to promote hair growth by providing a composition that can be applied topically or that can be produced in an ingestible form.

Another object of this invention is to provide a non-drug composition and method for the prevention of hair loss that can be used by both men and women safely and without irritation or harmful side effects.

Yet another object of this invention is to provide a composition to prevent hair loss that contains a substantial source of biologically-available silicon that can be absorbed by hair, the dermis, and the epidermis.

Still another object of the invention is to provide a non-drug alternative for inhibiting the formation of DHT in the skin and hair follicles of the scalp.

BRIEF DESCRIPTION OF THE DRAWINGS

FIG. 1b is a perspective drawing of the same scalp based on an actual photograph taken three days later than FIG. 1a.

FIGS. 2 through 4 show two tables and a chart summarizing the results obtained in the clinical trial study for Complex 1.

DETAILED DESCRIPTION

Figure 1B:
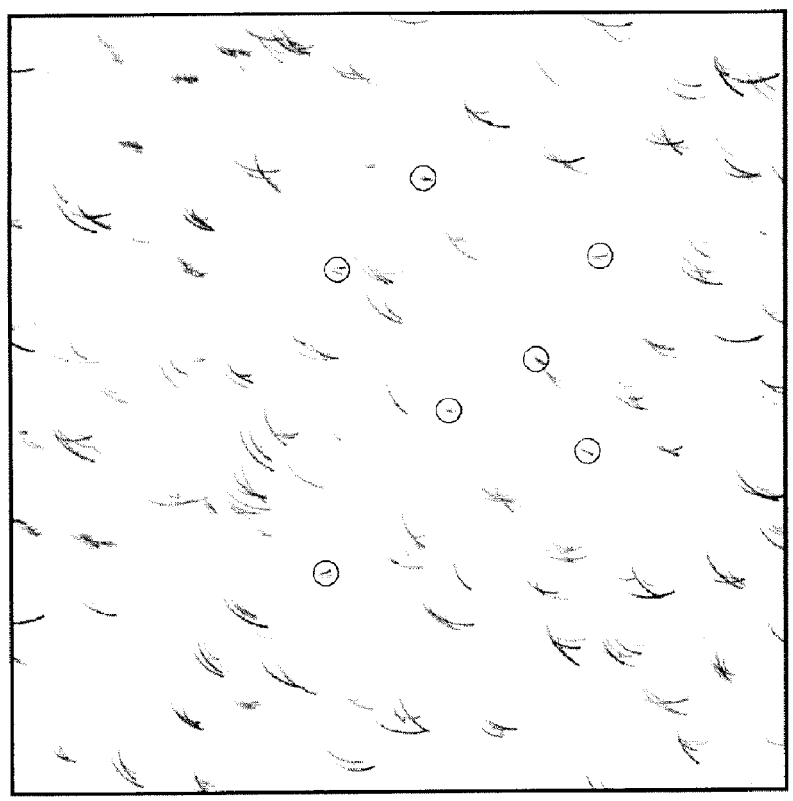

This invention is for a composition of matter to prevent hair loss and promote hair growth in humans that can be applied topically to the hair and scalp or ingested in the form of a dietary supplement, and a method for its use. The composition comprises a mixture of four complexes and a carrier liquid. Complex 1 is comprised of a mixture of octyl butyrate and glutaminpeptides. Octyl butyrate stimulates the synthesis of transglutaminase in keratinocytes as well as the formation of the cornified envelope of corneocytes. The transglutaminase synthesized in the scalp as a result of the presence of octyl butyrate then acts on the substrate of glutaminpeptides provided in Complex 1 to crosslink structural proteins in the hair through the formation of peptide bonds between the glutamine and lysine residues of the various structural proteins in hair. The crosslinking effect of the transglutaminase helps to more effectively anchor the hair to its site of attachment, thereby preventing hair loss. The glutaminpeptides used in Complex 1 are of cereal origin and are rich in glutamine. To maintain its stability against hydrolysis, glutamine is attached to a peptide chain of variable length, which results in the formation of the glutaminpeptide. Preferably, Complex 1 contains 1% octyl butyrate, 1% glutaminpeptide, and 98% carrier liquid by weight. Complex 1 is included in the composition at 0.05-8.0% by weight, but preferably 0.5-5.0%, and more preferably at 2.0-3.5% by weight.

EXAMPLE 1

In vivo tests were conducted to evaluate the efficacy of Complex 1 for purposes of hair loss prevention in persons presenting a high level of telogen phase hairs. Twenty male volunteers between the ages of 18 and 60 were selected from a recruited panel. In addition to meeting the usual inclusion criteria (good health, comprehension of the protocol) and exclusion criteria (no serious illness, ongoing treatment, cutaneous pathologies of the scalp, recent cosmetic treatments such as perms, dying, or minoxidil usage), volunteers exhibiting excessive hair loss were selected for participation. From among the recruited panel, twenty volunteers presenting less than 85% anagen hair, and preferentially less than 80% anagen hair, were retained. The usage of other hair care products was not allowed during the study To determine the effectiveness of Complex 1 in hair loss prevention, a photo-trichogram method was used which permitted analysis of hair on the scalp in terms of number of hairs per specified surface area and of the distribution of percentages of hair in anagen phase (the growth stage) and in telogen phase (the rest phase).

For each volunteer participating in the test, the hair was cut very close to the skin surface on a defined patch (5 mm×5 mm) of the scalp. This zone was then photographed with a macrophotolens to enable the counting of the number of hairs and their individual implantation in the skin. The images were analyzed by a computerized image analysis system. After three days, the participants came back for a second series of photographs of the same zones. Thereafter, the 20 participants received a lotion for friction that they used daily for three months by applying approximately 5 ml of the lotion to the scalp by a soft massage without rinsing. One lotion comprised a placebo which was given to a control group of 10 volunteers while the other "hair loss prevention" lotion containing 3% Complex 1 was given to a test group of 10 volunteers. The placebo and Complex 1 lotions were distributed randomly and without informing the participants as to which lotion each was using. After three months of treatment with the lotions, the same protocol for zone definition wherein a defined patch of hair was cut and photographed was repeated within a 3-day interval.

Comparison of the photographs taken between Day 0 and Day 3 and those taken between Day 90 and Day 93 allowed an estimation of total number of hairs, the number of hairs in anagen or telogen phase, and any improvements of the general state of the hair. Before beginning the treatment and after the end of the study, the volunteers completed a questionnaire concerning their evaluation and subjective appreciation of the products and the treatment. One participant did not return for the photograph session at the end of the study and another had to discontinue participation due to unrelated health problems. Therefore, the data analysis was based upon 9 volunteers having used the placebo lotion and 9 volunteers having used the hair loss prevention lotion containing 3% Complex 1.

Figure 1A:
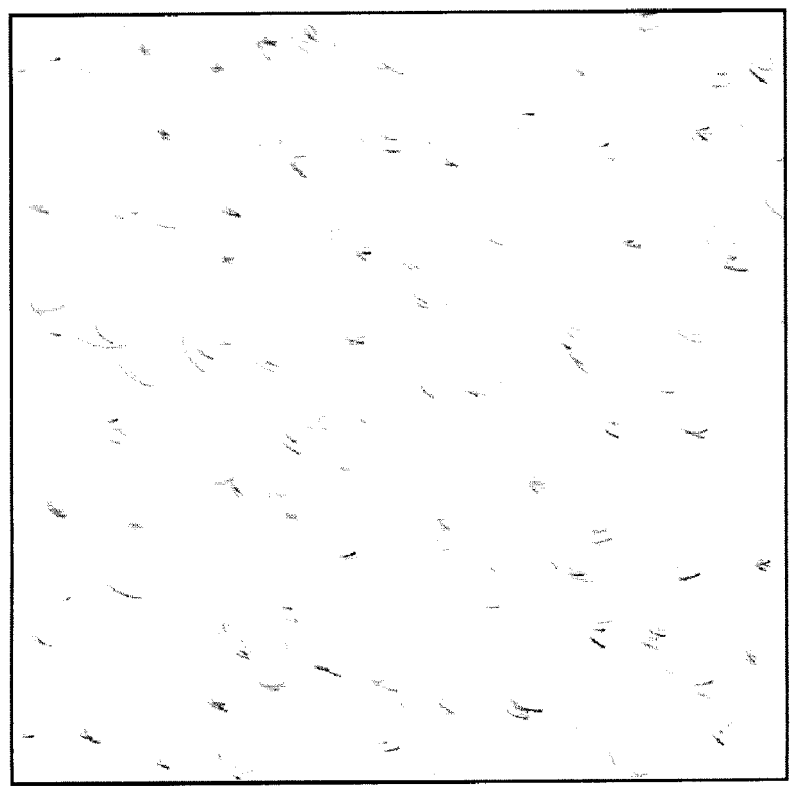
FIG. 1a shows a perspective drawing based on an actual photograph of a human scalp where the hair was cut close.

As an example, the drawings in FIG. 1a and FIG. 1b (based on actual photographs) illustrate the difference in hair length (anagen growth) during a three-day period. FIG. 1a is a human scalp where the hair was cut close and shows the hair in the anagen growth phase. FIG. 1b represents the same area of human scalp as in FIG. 1a but after a three-day period. The circled hairs that have not grown during this three-day period are shown in telogen phase in FIG. 1b. Eight out of nine participants (89%) who received the lotion containing Complex 1 exhibited a significant increase in the number of hairs in anagen phase (on average +12%, $p=0.016$, $T=3.09$) and a corresponding decrease in the number of telogen phase hairs (on average −30%, $p=0.01$, $t=3.39$) in 7 out of the 9 volunteers (78%). The changes observed after the remaining participants used the placebo lotion were not significant ($p>0.05$), with no notable increase in the distribution of hair in telogen phase. FIGS. 2 through 4 illustrate the results obtained in the clinical trial study for Complex 1. FIG. 2 shows the number of hairs in anagen phase and telogen phase at Day 0 and at Day 90 after application of the 3% Complex 1 lotion. FIG. 3 displays the number of hairs in anagen phase and telogen phase at Day 0 and at Day 90 after application of the placebo lotion. FIG. 4 shows the percentage of hair in telogen phase both before and after volunteers received treatment with the 3% Complex 1 lotion and the placebo lotion.

Analysis of the participants' subjective evaluation questionnaire answers produced the following observations: before treatment, a majority of the volunteers who used Complex 1 presented average quantities of dandruff and normal seborrheic state, and 67% of these participants demonstrated visible alopecia. For the Complex 1 test group, the amount of hair loss was strong for 22%, average for 67% and small for 11% (1 volunteer).

After three months of using the hair loss prevention lotion containing 3% Complex 1, the amount of hair loss appeared small to 44% (as opposed to 11% before the treatment) and average for 56% of the test group participants. Overall, 67% of the test group volunteers observed a decrease in hair loss.

Before treatment, the majority of the control group volunteers presented average quantities of dandruff and normal seborrheic state. Of these participants, 77% demonstrated visible alopecia. The amount of hair loss was average for 66% and small for 33% of the control group. After three months of using the placebo lotion, the amount of hair loss appeared unchanged in the control group (small for 33% and average for 66%). The control group participants did not observe any notable improvement in their alopecia.

Complex 2 contains a mixture of copper ion, red saw palmetto extract, pygeum extract, nettle extract, zinc, vitamin B6, and linolenic acid, all of which have demonstrated excellent hair loss preventative properties. Copper ion inhibits the action of Type 1 and Type 2 5-alpha-reductase, thereby blocking the formation of DHT in the skin and hair follicles. Copper ion is included in the composition at 0.001-4.0% by weight, but preferably 0.01-1.0%, and more preferably at 0.4-0.7% by weight. Extract of the berries of red saw palmetto (*Serenoa repens*) also blocks 5-alpha-reductase from stimulating the production of DHT in the hair follicles and skin. Both the copper ion and the saw palmetto extract reduce DHT binding at its receptor sites in the skin by 50%. The extracts of pygeum bark (*Pygeum africanum*) and nettle root (*Urtica dioica*) inhibit 5-alpha-reductase and aromatase, enzymes critical to DHT production, and taken together exhibit a synergy that increases the effectiveness of each extract. Red saw palmetto extract, pygeum extract, nettle extract are included in the composition at 0.05-5.0% by weight, but preferably 0.5-2.0%, and more preferably at 1.0-1.5% by weight.

Gamma linolenic acid, an unsaturated fatty acid included in Complex 2, also inhibits 5-alpha-reductase and DHT production. Linolenic acid is included in the composition at 0.05-5.0% by weight, but preferably 0.5-2.0%, and more preferably at 1.0-1.5% by weight.

Zinc and vitamin B6 are excellent 5-alpha-reductase inhibitors. When the level of vitamin B6 in the skin is increased, cells become less responsive to hormones that can cause androgenic alopecia as well as other disorders related to DHT. Vitamin B6 and zinc work synergistically when combined to inhibit the body's conversion of testosterone to DHT. However, the level of zinc must be closely controlled due to its propensity to replace copper in the scalp. Without an adequate supply of copper, angiogenesis (new blood vessel formation) will not occur, and the scalp can be damaged. Zinc and vitamin B6 are each included in the composition at 0.01-4.0% by weight, but preferably 0.1-1.0%, and more preferably at 0.4-0.7% by weight.

Additionally, Complex 2 may also contain butyl avocadate, zinc PCA, and licorice extract, all of which are effective 5-alpha-reductase inhibitors. If included, these compounds are to be present in the composition at 0.05-5.0% by weight, but preferably 0.5-2.0%, and more preferably at 1.0-1.5% by weight.

Complex 3 comprises *Ginkgo biloba*, emu oil, a biologically available source of silicon, and a blend of sulfur-containing amino acids. *Ginkgo biloba*, which is known to improve blood circulation, has been reported to inhibit 5-alpha-reductase conversion of testosterone to DHT. Emu oil, which contains a high level of linolenic acid, increases the thickness of the skin as well as the size of hair follicles. *Ginkgo biloba* is included in the composition at 0.05-5.0% by weight, but preferably 0.5-2.0%, and more preferably at 1.0-1.5% by weight. Emu oil is included in the composition at 0.05-6.0% by weight, but preferably 0.5-3.0%, and more preferably at 1.5-2.0% by weight.

Complex 3 also contains a novel source of bioavailable silicon prepared by the mild hydrolysis of dimethylsilyl salicylate. The resulting silanol is created by electro-osmosis wherein a glass vessel (made from silica) forms the stationary charged surface. When silica is in contact with an aqueous solution of dimethylsilyl salicylate in the presence of a minor amount of alcohol, the surface of the silica hydrolyzes to form charged silanol groups. At pH 7.4, these charged silanol surface groups will hydrolyze to form SiO—. The negatively charged SiO— groups will attract positively charged ions and repel negatively charged ones in the solution, causing a buildup of positive charges near the inner surface of the beaker or vessel to form an electric double layer. This double layer becomes the finished silanol, which is a silicon analogue of alcohol. In this composition, silanol provides human hair with a source of biologically-useable silicon that has numerous hydroxyl functional groups. The quantity and quality of hair is dependent upon the amount of silicon available for biological usage (most silicon, consumed in the form of silica, is not useable by the human body). Silanol is included in the composition at 0.001-4.0% by weight, but preferably 0.01-1.0%, and more preferably at 0.3-0.5% by weight.

EXAMPLE 2

Clinical studies were conducted to test the efficacy of the novel silanol. Short-term studies were conducted during six-week trial periods with healthy male and female volunteers. Treatment 1, comprised of 0.05% silanol, was used by 12 volunteers between the ages of 19 and 37. Treatment 2, comprised of 0.03% silanol, was used by 12 volunteers between the ages of 20 and 41. Treatment 3, comprised of 0.05% silanol, was used by 18 volunteers between the ages of 18 and 52. In each treatment group, the volunteers applied a lotion containing the silanol active ingredient twice each day during the six-week test period. The results of the short-term studies are described below.

Concerning hair loss evolution, 67% of the volunteers in Treatment 1 group reported an important improvement while 33% reported a slight improvement. All of the volunteers in Treatment 1 group reported that the lotion had a positive influence on hair growth. In addition, 90% of volunteers in Treatment 1 group reported a positive effect on the general aspect of the hair while 10% reported that the lotion had no effect. The general aspect of the hair is defined as the feelings of a volunteer regarding the overall improvement in the quality of his or her hair after use of the silanol lotion.

Treatment 2 group reported improvement in hair loss evolution among 68% of its volunteers and no effect among the remaining 32%. Treatment 2 group also reported that the lotion had a positive influence on hair growth in 38% of the volunteers and no effect among the remaining 62%. Furthermore, 68% of volunteers in the Treatment 2 group reported that the lotion had a positive effect on the general aspect of the hair, 15% reported a negative effect, and 21% reported no effect.

After using the lotion, 74% of volunteers in Treatment 3 group reported an important improvement in hair loss evolution, 23% reported a slight improvement, and 4% reported that the lotion had no effect. Treatment 3 group also reported a positive influence on hair growth among 96% of the volunteers while 4% reported no effect on hair growth. All of the volunteers in Treatment 3 group reported a positive effect on the general aspect of the hair.

In addition, a long-term study was conducted for five months with 45 volunteers who applied the lotion to their scalps twice each day. The lotion used in this long-term study contained 0.05% silanol, and the results were confirmed by subjective assessment of videotrichograms. The results of this study indicated that the silanol-containing lotion stopped additional hair loss, increased the amount of hair in anagen phase, increased hair growth, and decreased seborrhea in the volunteers.

A blend of sulfur-containing amino acids, including taurine, cysteine, methionine, and glutathione, are also included as components of Complex 3. These amino acids are considered essential for hair growth as they bond together to form most of the structural proteins of which hair consists. Cysteine, a sulfur-containing amino acid present in high levels in human hair, has been found to produce significant modification in wool growth patterns when given as a supplement in the diet of sheep and has produced thicker hair shafts in rats during experiments. The Complex 3 amino acids may be applied topically and are also ingestible. Each of these amino acids is included in the composition at 0.05-5.0% by weight, but preferably 0.5-2.0% by weight, and more preferably at 1.0-1.5% by weight.

Complex 4 provides the composition with its hair growth-promoting properties, and comprises extracts of bergamot, jaborandi, southernwood, and nettle. Other hair growth stimulants that may also be used in Complex 4 in addition to those already named above include, but are not limited to, *Swertia japonica, ginseng,* myrrh, quillaia, sandalwood, basil, and rosemary. All of the components comprising Complex 4 are present in the composition at 0.05-5.0% by weight, but preferably 0.5-2.0% by weight, and more preferably at 1.0-1.5% by weight.

Table 1, below, summarizes the preferred and more preferred embodiments of this composition as it pertains to the quantities in percent by weight of each component of said composition.

| Component | Quantity (percent by weight) Preferred | Quantity (percent by weight) More Preferred |
| --- | --- | --- |
| Complex 1 | 0.5-5.0 | 2.0-3.5 |
| Silicon (as Silanol) | 0.01-1.0 | 0.3-0.5 |

-continued

| Component | Quantity (percent by weight) Preferred | Quantity (percent by weight) More Preferred |
| --- | --- | --- |
| Copper Ion | 0.01-1.0 | 0.4-0.7 |
| Saw Palmetto | 0.5-2.0 | 1.0-1.5 |
| Pygeum | 0.5-2.0 | 1.0-1.5 |
| Nettle | 0.5-2.0 | 1.0-1.5 |
| Linolenic Acid | 0.5-2.0 | 1.0-1.5 |
| Zinc | 0.1-1.0 | 0.4-0.7 |
| Vitamin B6 | 0.1-1.0 | 0.4-0.7 |
| Ginkgo biloba | 0.5-2.0 | 1.0-1.5 |
| Cysteine | 0.5-2.0 | 1.0-1.5 |
| Taurine | 0.5-2.0 | 1.0-1.5 |
| Methionine | 0.5-2.0 | 1.0-1.5 |
| Glutathione | 0.5-2.0 | 1.0-1.5 |
| Emu Oil | 0.5-3.0 | 1.5-2.0 |
| Bergamot | 0.5-2.0 | 1.0-1.5 |
| Jaborandi | 0.5-2.0 | 1.0-1.5 |
| Southernwood | 0.5-2.0 | 1.0-1.5 |
| Swertia japonica | 0.5-2.0 | 1.0-1.5 |
| Ginseng | 0.5-2.0 | 1.0-1.5 |
| Licorice | 0.5-2.0 | 1.0-1.5 |
| Zinc PCA | 0.5-2.0 | 1.0-1.5 |
| Butyl avocadate | 0.5-2.0 | 1.0-1.5 |
| Carrier liquid | Remainder | Remainder |

The four complexes are mixed together (using standard mixing techniques known to one skilled in the art) with a carrier liquid comprised of water, a 10% (by weight) surfactant, and either propylene glycol or glycerine. The composition can be added to any topical treatment, such as a shampoo, conditioner, styling product, or serum, or can be ingested in the form of a dietary supplement, such as a caplet, tablet, capsule, lozenge, or drink. The preferred embodiment of the invention is that the composition be applied topically to the scalp and hair in the form of a serum. The product should be used by the consumer at regular intervals twice each day for the first 7 days and then preferably 5 to 7 times per week, and more preferably 7 times per week. Preferably, the use of the serum will be supplemented by the consumer's use of the composition in the form of a shampoo and as a dietary supplement to further enhance the serum's effects. The shampoo and dietary supplement would be used simultaneously with the serum's daily application.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A composition of matter for the prevention of hair loss and the promotion of hair growth to be applied topically to the hair and scalp comprising a mixture of the following:
   a. Complex 1: a mixture of glutamine-containing peptides and octyl butyrate;
   b. Complex 2: a mixture of copper ion, red saw palmetto extract, pygeum extract, nettle extract, zinc, vitamin B6, and linolenic acid;
   c. Complex 3: a mixture of *Ginkgo biloba* extract, emu oil, a source of biologically-useful silicon in the form of a silanol, and a blend of amino acids;
   d. Complex 4: a mixture of extracts of bergamot, jaborandi, southernwood, and nettle; and
   e. a carrier liquid.

2. The invention according to claim 1, wherein the carrier liquid is comprised of water, a surfactant in the amount of 10% by weight of the composition, and propylene glycol or glycerine.

3. The invention according to claim 1, wherein Complex 1 comprises preferably 1% octyl butyrate, 1% glutamine-containing peptides, and 98% the carrier liquid by weight.

4. The invention according to claim 1, wherein the percent by weight quantities for each ingredient in the composition are 0.05-8.0% Complex 1; 0.01-4.0% silanol; 0.001-4.0% copper ion; 0.05-5.0% red saw palmetto; 0.05-5.0% pygeum; 0.05-5.0% nettle; 0.05-5.0% linolenic acid; 0.01-4.0% zinc; 0.01-4.0% vitamin B6; 0.05-5.0% *Ginkgo biloba;* 0.05-5.0% cysteine; 0.05-5.0% taurine; 0.05-5.0% methionine; 0.05-5.0% glutathione; 0.05-6.0% emu oil; 0.05-5.0% bergamot; 0.05-5.0% jaborandi; 0.05-5.0% southernwood; and the carrier liquid as the remainder.

5. The invention according to claim 1, wherein the preferred percent by weight quantities for each ingredient in the composition are 0.5-5.0% Complex 1; 0.1-1.0% silanol; 0.01-1.0% copper ion; 0.5-2.0% red saw palmetto; 0.5-2.0% pygeum; 0.5-2.0% nettle; 0.5-2.0% linolenic acid; 0.1-1.0% zinc; 0.1-1.0% vitamin B6; 0.5-2.0% *Ginkgo biloba;* 0.5-2.0% cysteine; 0.5-2.0% taurine; 0.5-2.0% methionine; 0.5-2.0% glutathione; 0.5-3.0% emu oil; 0.5-2.0% bergamot; 0.5-2.0% jaborandi; 0.5-2.0% southernwood; and the carrier liquid as the remainder.

6. The invention according to claim 1, wherein the more preferred percent by weight quantities for each ingredient in the composition are 2.0-3.5% Complex 1; 0.3-0.5% silanol; 0.4-0.7% copper ion; 1.0-1.5% red saw palmetto; 1.0-1.5% pygeum; 1.0-1.5% nettle; 1.0-1.5% linolenic acid; 0.4-0.7% zinc; 0.4-0.7% vitamin B6; 1.0-1.5% *Ginkgo biloba;* 1.0-1.5% cysteine; 1.0-1.5% taurine; 1.0-1.5% methionine; 1.0-1.5% glutathione; 1.5-2.0% emu oil; 1.0-1.5% bergamot; 1.0-1.5% jaborandi; 1.0-1.5% southernwood; and the carrier liquid as the remainder.

7. The invention according to claim 1, wherein the blend of amino acids comprises cysteine, taurine, methionine, and glutathione.

8. A method to prevent hair loss and promote hair growth comprising applying to the hair and scalp a composition comprising a mixture of Complexes 1, 2, 3, and 4, as those Complexes are described in claim 1, and a carrier liquid.

9. The method according to claim 8, wherein the composition is added to any topical treatment, such as a shampoo, conditioner, styling product, or serum, that is to be applied to the scalp and hair twice each day for the first 7 days of use, and thereafter, 5 to 7 times per week.

10. The method according to claim 8, wherein the composition is produced in the form of an ingestible dietary supplement, such as a caplet, tablet, capsule, lozenge, or drink that is to be taken twice each day for the first 7 days of use, and thereafter, 5 to 7 times per week.

11. The method according to claim 8, wherein the composition preferably is applied topically to the hair and scalp in the form of a serum.

12. The method according to claim 8, wherein the composition is preferably applied to the scalp and hair in the form of a serum twice each day for the first 7 days of use, and thereafter, 7 times per week.

13. The method according to claim 8, wherein the composition preferably is applied topically to the hair and scalp in the form of a serum twice each day for the first 7 days of use, and thereafter, 7 times per week, and is supplemented by use of the composition in the form of a shampoo or an ingestible dietary supplement.

* * * * *